United States Patent [19]

Strong

[11] Patent Number: 5,122,608

[45] Date of Patent: Jun. 16, 1992

[54] METHOD FOR THE PREPARATION OF SUBSTITUTED AND UNSUBSTITUTED 2,3-PYRIDINE AND QUINOLINEDICARBOXYLIC ACIDS

[75] Inventor: Henry L. Strong, Somerset, N.J.

[73] Assignee: American Cyanamid Company, Stamford, Conn.

[21] Appl. No.: 631,594

[22] Filed: Dec. 19, 1990

[51] Int. Cl.$^5$ ............... C07D 213/803; C07D 215/16
[52] U.S. Cl. .................... 546/170; 546/321; 546/168; 546/171; 546/176
[58] Field of Search ................... 546/170, 321

[56] References Cited

U.S. PATENT DOCUMENTS

| | | | |
|---|---|---|---|
| 3,027,380 | 3/1962 | Leonard et al. | 260/295.5 |
| 3,829,432 | 8/1974 | Hanotier et al. | 260/295.5 |
| 4,460,776 | 7/1984 | Wepplo | 546/250 |
| 4,608,079 | 8/1986 | Los | 71/97 |
| 4,723,011 | 2/1988 | Doehner, Jr. | 546/250 |
| 4,798,619 | 1/1989 | Los | 71/66 |

FOREIGN PATENT DOCUMENTS

| | | |
|---|---|---|
| 292032A | 11/1988 | European Pat. Off. . |
| 299362A | 1/1989 | European Pat. Off. . |
| 3150005 | 6/1983 | Fed. Rep. of Germany . |
| 3345223 | 6/1985 | Fed. Rep. of Germany . |
| 2193820 | 2/1974 | France . |
| 880592 | 10/1961 | United Kingdom . |

OTHER PUBLICATIONS

Hoogeweff et al., Chem. Ber., 13: 1639.
Riedel, Chem. Ber., 16: 1609-1616 1639.
Doebner et al., Chem. Ber., 18: 1640-1646—1613.
Monatshefte Fur Chem., 3:79 11639.
Oakes et al., J. Chem. Soc., p. 4433 (1956).
Blank et al., J. Medicinal Chem., 17 (No. 10): 1065-(1974).

*Primary Examiner*—David B. Springer
*Attorney, Agent, or Firm*—Alice C. Brennan

[57] ABSTRACT

There is provided a process for the preparation of a substituted or unsubstituted 2,3-pyridine or quinolinedicarboxylic acid by hydrolysis of a substituted or unsubstituted 2,3-pyridine or quinolinedicarboxylic acid diester with an acid having an ionization constant $pK_a$ of less than 3.0 followed by isolation of the product as the free acid or an acid salt.

10 Claims, No Drawings

METHOD FOR THE PREPARATION OF SUBSTITUTED AND UNSUBSTITUTED 2,3-PYRIDINE AND QUINOLINEDICARBOXYLIC ACIDS

BACKGROUND OF THE INVENTION

The discovery, development and commercialization of the 2-(2-imidazolin-2-yl) pyridines and quinolines as herbicidal agents has given new meaning to the term "weed control"; for within this series of compounds it has been found that some are broad-spectrum or total vegetation herbicides with activity in both herbaceous and woody plants. Others are highly selective weed control agents useful as weed control agents in the presence of crops. The broad-spectrum compounds have been widely accepted for use in cleaning industrial sites and rights-of-way for railroads and power lines while the selective herbicides are used extensively as weed control agents in the presence of soybeans, snapbeans, peas and alfalfa. Such acceptance has stirred the interest of many researchers in the field of agricultural chemistry and has led to development of a variety of synthetic routes to the preparation of the herbicidally active 2-(2-imidazolin-2-yl)pyridines and quinolines.

Several of these processes involve the preparation of 2,3-pyridinedicarboxylic acid anhydrides from 2,3-pyridinedicarboxylic acids, but methods for the preparation of the 2,3-pyridinedicarboxylic acids are rather limited and those processes that are available may be arduous, time-consuming or multi-step processes that are not entirely satisfactory.

For example, P. J. Wepplo in U.S. Pat. No. 4,460,776, describes the preparation of a 6-substituted-2,3-pyridinedicarboxylic acid diester and the hydrolysis of the diester to the corresponding diacid by reaction of the diester with strong base in the presence of alcohol. Thereafter, the reaction mixture is treated with a strong mineral acid, ice and an alcohol. The mixture is then cooled, diluted with a ketonic solvent, treated with solid sodium sulfate and filtered. The filtrate is concentrated, the residue triturated with ether and the diacid removed by filtration. Treatment of the diacid with acetic anhydride in the presence of dimethoxyethane and pyridine yields the 6-substituted-2,3-pyridinedicarboxylic acid anhydride which is further treated to obtain the herbicidal 6-substituted-2-(5-isopropyl-5-methyl-4-oxo-2-imidazolin-2-yl)nicotinic acid.

M. Los in U.S. Pat. No. 4,608,079 discloses the preparation of 3-chloro-4-methylphthalic acid from 3-chloro-N,N-diethyl-p-toluamide using butyl lithium in cyclohexane in the presence of anhydrous tetrahydrofuran and $N,N,N^1,N^1$-tetramethylethylenediamine.

R. F. Doehner, Jr., in U.S. Pat. No. 4,723,011, discloses the preparation of substituted and disubstituted pyridine-2,3-dicarboxylate esters. However, the patentee also discloses the base hydrolysis of the diester described by Wepplo for the preparation of the substituted or disubstituted diacid, followed by conversion of the diacid to the anhydride. The anhydride is then reacted with an aminocarboxamide or aminothiocarboxamide to form the pyridine monoacid-diamide which is cyclized to the active substituted or disubstituted 2-(5-isopropyl-5-methyl-4-oxo-2-imidazolin-2-yl)nicotinic acid.

Methods requiring the use of transition metal catalysts in oxidizing quinolines such as those described in German Patents 3,345,223 and 3,150,005; French Patent 2,193,820; and U.S. Pat. No. 3,829,432 are limited to the preparation of either the unsubstituted 2,3-pyridinedicarboxylic acid or to the preparation of those compounds which do not contain substituents which are also oxidized during the process. Additionally, an oxidative method for the preparation of 2,3-pyridinedicarboxylic acids is disclosed in U.S. Pat. No. 3,027,380 which describes the preparation of 5-fluoropyridine-2,3-dicarboxylic acid by the action of nascent or atomic oxygen on 3-fluoroquinoline; and British Patent Application 880,592 describes a method of preparing substituted and unsubstituted 2,3-pyridinedicarboxylic acids by ozonolysis of benzazines such as quinalidine, lepidine, carbostyril, 8-hydroxyquinoline and 2-aminoquinoline in the presence of a sufficient amount of a mineral acid such as nitric acid, sulfuric acid or phosphoric acid to form a salt of the benzazine.

Early reports describing the preparation of alkyl substituted 2,3-pyridinedicarboxylic acids by oxidative methods stemmed from interest in lepidine (4-methylquinoline).

S. Hoogeweff and W. A. van Dorp *Chem. Ber.* 13, 1639 reported that 4-methyl-2,3-pyridinedicarboxylic acid may be isolated from the stepwise oxidation of lepidine with permanganate.

C. Riedel, *Chem. Ber.* 16 1609–1616 citing the work of Hoogeweff and van Dorp, proposed in a like manner to conduct a reaction sequence of oxidizing $\beta$-ethylbenzoquinoline to $\beta$-ethylpyridine-2,3-carboxylic acid, followed by decarboxylation by distillation over calcium hydroxide to obtain $\beta$-ethylpyridine which would, upon further oxidation yield $\beta$-pyridinecarboxylic acid, as a method to confirm the position of the carboxlyic acid substituent.

Riedel reported that oxidation of $\beta$-ethylbenzoquinoline with chromic acid yielded $\beta$-benzoquinolinecarboxylic acid and that further oxidation of this compound with potassium permanganate under basic conditions yielded the corresponding pyridinetricarboxylic acid. Based upon this result, Riedel drew the conclusion that the difference in behavior of $\beta$-ethylquinoline and lepidine was due to the difference in the length of the alkyl chain (ethyl vs methyl).

O. Doebner and W. van Miller *Chem. Ber.* 18, 1640–1646, commented on the conclusion drawn by Riedel, citing H. Weidel. Monatshefte F. Chem. 3 79 "who showed that, in the oxidation of cincholepidine with chromic acid instead of with potassium permanganate, it is not the benzene group but the methyl group that is attacked". Doebner and van Miller additionally demonstrated that the oxidation $\beta$-methylquinoline with chromic acid also resulted in oxidation of the methyl group.

Support for the Doebner and van Miller publication has been evidenced by the potassium permanganate oxidation of 3-ethylquinoline under basic conditions (the conditions employed by Riedel for the subsequent oxidation $\beta$-benzoquinolinecarboxylic acid to the corresponding pyridinetricarboxylic acid) to produce 5-ethylpyridine-2,3-dicarboxylic acid in 6 to 7% yields.

Recent oxidative methods which have been reported to be suitable for the preparation of 2,3-pyridinedicarboxylic acids containing substituents in the 4, 5 and 6 position of the pyridine ring include:

A. the preparation of 5-methylpyridine-2,3-dicarboxylic acid by nitric acid oxidation of 8-hydroxy-3-methylquinoline which was obtained by Skraup reaction of o-aminophenol with α-methylacraldehyde; V. Oakes and H. N. Rydon, *J. Chem. Soc.*, 4433 (1956); and B. the preparation of 4-methylpyridine-2,3-dicarboxylic acid, in 65% yield; 5-methylpyridine-2,3-dicarboxylic acid, in 50% yield; and 6-methylpyridine-2,3-dicarboxylic acid in 57% yield by the oxidation of the corresponding 4, 5 or 6 methyl 8-hydroxyquinoline with nitric acid and the preparation of 5-chloropyridine-2,3-dicarboxylic acid in 31% yield by the oxidation of 3-chloroquinoline with KMnO₄; B. Blank, et al., *J. Med. Chem.*, Vol 17, No. 10, 1065 (1974).

It has been shown that oxidation 3-ethyl-8-hydroxyquinoline (prepared in 39% yield by the Skraup reaction of o-aminophenol with 2-ethylacrolein), with nitric acid as described in the above publications yields: 5-ethyl-2,3-pyridinedicarboxylic acid having mp 146°-147° C. in 40% yield.

Like the processes of the patent art, the methods of synthesis of the 2,3-pyridine and quinolinedicarboxylic acids described in the literature are not entirely satisfactory for large scale commercial production.

It is therefore an object of the present invention to provide an effective and efficient method for the preparation of substituted and unsubstituted 2,3-pyridine and quinolinedicarboxylic acids.

SUMMARY OF THE INVENTION

The present invention is directed to a method for the preparation of substituted and unsubstituted 2,3-pyridine and quinolinedicarboxylic acids of formula I

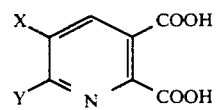

wherein X and Y are each independently hydrogen, halogen, $C_1$-$C_6$ alkyl, $C_1$-$C_4$ hydroxyalkyl, $C_1$-$C_4$ alkoxyalkyl, $C_1$-$C_6$ alkoxy, $C_1$-$C_4$ alkylthio, phenoxy, $C_1$-$C_4$ haloalkyl, nitro, cyano, $C_1$-$C_4$ alkylamino, diloweralkylamino, $C_1$-$C_4$ alkylsulfonyl or phenyl optionally substituted with a $C_1$-$C_4$ alkyl, $C_1$-$C_4$ alkoxy or halogen group; and, when taken together, X and Y may form a ring in which XY is represented by the structure

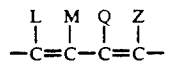

wherein L, M, Q and Z are each hydrogen, halogen, $C_1$-$C_4$ alkyl or $C_1$-$C_4$ alkoxy; by hydrolyzing a 2,3-pyridine or quinolinedicarboxylic acid diester of formula II

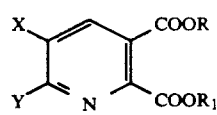

wherein R and $R_1$ each represent a $C_1$-$C_6$ alkyl group and X and Y are as described above for formula I; by heating the dicarboxylic acid diester in the presence of water and an acid having an ionization constant $pK_a$ of less than 3.0 at a temperature between about 50° C. and 110° C., separating water and alcohol from the reaction mixture, cooling the remaining reaction mixture to a temperature between about 20° C. and 35° C., treating the remaining reaction mixture with base, if the reaction mixture has a pH value less than pH 1.3, to adjust the pH of said mixture to a value between 1.3 and 2.0 and separating the formula I 2,3-pyridine or quinolinedicarboxylic acid from the pH adjusted mixture.

DETAILED DESCRIPTION OF THE INVENTION

One of the embodiments of the present invention relates to a method for the preparation of acid salts of formula I substituted and unsubstituted 2,3-pyridine and quinolinedicarboxylic acids by hydrolyzing a formula II 2,3-pyridine or quinolinedicarboxylic acid diester in the presence of water and an acid having a $pK_a$ of less than 3.0 at a temperature between about 50° C. and 110° C., cooling the heated mixture to a temperature between about 20° C. and 40° C., washing the cooled mixture with a volatile chlorinated hydrocarbon, an ether or a water-immiscible alcohol, adding to the washed mixture 1,1'-oxybis[2-methoxyethane]; 2,5,8,11-tetraoxadodecane or 2,5,8,11,14-pentaoxapentadecane and separating water to obtain the formula I 2,3-pyridine or quinolinedicarboxylic acid as the acid salt and optionally dispersing said acid salt in water or aqueous base to obtain the formula I 2,3-pyridine or quinolinedicarboxylic acid.

The method of the present invention is especially efficacious for the preparation of 5-ethyl-2,3-pyridinedicarboxylic acid, 2,3-pyridinedicarboxylic acid, 5-methoxymethyl-2,3-pyridinedicarboxylic acid, 5-methyl-2,3-pyridinedicarboxylic acid and 2,3-quinolinedicarboxylic acid.

The product formula I 2,3-pyridine and quinolinedicarboxylic acids may be isolated by filtration of the formula I product or by extraction of the reaction mixture with a suitable solvent. In the isolation procedure suitable extraction solvents include tetrahydrofuran and water-immiscible alcohols.

Acids having an ionization constant $pK_a$ of greater than 3.0 are unable to fully protonate the pyridine or quinoline ring of a formula I 2,3-pyridine or quinolinedicarboxylic acid. This lack of protonation leads to decomposition of the desired formula I dicarboxylic acid through decarboxylation. Therefore, it is desirable to employ acids having an ionization constant $pK_a$ of less than 3.0 to avoid this unwanted decarboxylation while effectively hydrolyzing formula II dicarboxylic diesters to the desired formula I dicarboxylic acids of the present invention.

Representative acids for use in the present invention include both mineral acids and organic acids having an ionization constant $pK_a$ of less than 3.0, as shown below, with sulfuric acid, hydrobromic acid and hydrochloric acid being preferred. At least 1.1 molar equivalents of the acid is required to hydrolyze a formula II dicarboxylic acid diester. Typically about 1.5 to 5 molar equivalents and preferably 3 to 5 molar equivalents of acid is employed to hydrolyze a formula II diester.

| Acid | $pK_a$ |
|---|---|
| Sulfuric | −3.0 |
| Sulfurous | 1.9 |
| Hydrochloric | −6.1 |
| Hydrobromic | −9.0 |
| Trifluoroacetic | 0.5 |
| Trichloroacetic | 0.5 |
| β-Naphthalene sulfonic | 0.6 |

-continued

| Acid | $pK_a$ |
|---|---|
| Benzene sulfonic | 2.6 |
| p-Toluene sulfonic | 0.9 |
| p-Ethylbenzene sulfonic | 0.9 |
| Dichloroacetic | 1.3 |
| Phosphoric | 2.5 |

Bases suitable for use in the present invention include aqueous bases such as alkali metal and alkaline earth metal hydroxides and carbonates with aqueous sodium hydroxide and potassium hydroxide being preferred.

Volatile chlorinated hydrocarbons suitable for use in the present invention include dichloromethane, carbon tetrachloride, chloroform, 1,2-dichloroethane, 1,1,1-trichloroethane and the like with dichloromethane being preferred. Ethers suitable for use in the present invention include diethyl ether, tetrahydrofuran and the like with tetrahydrofuran being preferred. Water-immiscible alcohols which may be employed in the method of the present invention include n-butanol, n-hexanol, n-pentanol and the like.

Water and alcohol form an azeotrope at elevated temperatures and this azeotrope is separated from the reaction mixture of the present invention by continuous distillation. Since the by-product alcohol is continuously separated from the reaction mixture, the reaction mixture is unable to establish an equilibrium and proceeds until all of the formula II dicarboxylic acid diester is hydrolyzed to the desired formula I 2,3-pyridine or quinolinedicarboxylic acid.

Acid salts of formula I 2,3-pyridine and quinolinedicarboxylic acids generally cannot be isolated from aqueous solutions. Therefore, when a high boiling solvent such as 1,1'-oxybis[2-methoxyethane], 2,5,8,11-tetraoxadodecane, 2,5,8,11,14-pentaoxapentadecane and the like is added to the washed reaction mixture of the present invention to allow for the separation of water via distillation at an elevated temperature and/or at reduced pressure. Since the water is now removed, the above acid salt may be isolated in high yield.

In order to facilitate a further understandin of the invention, the following examples are presented to illustrate more specific details thereof. The invention is not to be limited thereby except as defined in the claims.

EXAMPLE 1

Preparation of 5-Methoxymethyl-2,3-pyridinedicarboxylic acid using sulfuric acid A mixture of 5-methoxymethyl-2,3-pyridinedicarboxylic acid dimethyl ester (12.0 g, 0.05 mol), sulfuric acid (14.7 g, 0.15 mol) and water (40 g, 2.2 mol) is heated at 70° to 110° C. A mixture of methanol and water is continuously distilled from the reaction mixture and heating is continued until the reaction is complete by chromatographic analysis. The reaction mixture is cooled to room temperature and the pH is adjusted to 1.3 to 2.0 with 50% sodium hydroxide. The title product is isolated by filtration, washed with water (20 mL) and dried in vacuo. The title product is identified by $^1$HNMR and mass spectroscopy and analyzed by high pressure liquid chromatography to be >96% pure.

EXAMPLE 2

Preparation of 5-Methoxymethyl-2,3-pyridinedicarboxylic acid using hydrochloric acid A mixture of 5-methoxymethyl-2,3-pyridinedicarboxylic acid dimethyl ester (12.0 g, 0.05 mol), hydrochloric acid (9.1 g, 0.25 mol) and water (36 g) is heated at 70° to 110° C. A mixture of methanol, water and hydrochloric acid is continuously distilled from the reaction mixture, and heating is continued until the reaction is complete by chromatographic analysis. The reaction mixture is cooled to room temperature and the pH is adjusted to 1.3 to 2.0 with 50% sodium hydroxide. The title product is isolated by filtration, washed with water (20 mL) and dried in vacuo. The title product is identified by $^1$HNMR and mass spectroscopy and analyzed by high pressure liquid chromatography to be >92% pure.

EXAMPLE 3

Preparation of 5-Methyl-2,3-pyridinedicarboxylic acid using phosphoric acid

A stirred mixture of 5-methyl-2,3-pyridinedicarboxylic acid dimethyl ester (20.9 g, 0.1 mol), phosphoric acid (29.4 g, 0.3 mol) and water (60 g, 3.3 mol) is heated at 70° to 110° C. A mixture of methanol and water is continuously distilled from the reaction mixture and heating is continued until the reaction is complete by chromatographic analysis. The mixture is cooled to room temperature and the title product is allowed to precipitate. The title product is isolated by filtration, washed with water (30 mL) and dried in vacuo. The title product is identified by $^1$HNMR and mass spectroscopy and analyzed by high pressure liquid chromatography to be >97% pure.

EXAMPLE 4

Preparation of 5-Methyl-2,3-pyridinedicarboxylic acid using hydrochloric acid

A stirred mixture of 5-methyl-2,3-pyridinedicarboxylic acid dimethyl ester (20.9 g, 0.1 mol), hydrochloric acid (18.2 g, 0.5 mol) and water (72 g) is heated at 70° to 110° C. A mixture of methanol and water and hydrochloric acid is continuously distilled from the reaction mixture and heating is continued until the reaction is complete by chromatographic analysis. The reaction mixture is concentrated in vacuo and diluted with water. The title product is isolated by filtration, washed with water (30 mL) and dried in vacuo. The title product is identified by $^1$HNMR and mass spectroscopy and analyzed by high pressure liquid chromatography to be >96% pure.

EXAMPLE 5

Preparation of 5-Methyl-2,3-pyridinedicarboxylic acid using hydrobromic acid

A stirred mixture of 5-methyl-2,3-pyridinedicarboxylic acid dimethyl ester (20.9 g, 0.1 mol), hydrobromic acid (40.5 g, 0.5 mol) and water (50 g) is heated at 70° to 110° C. A mixture of methanol, water and hydrobromic acid is continuously distilled from the reaction mixture and heating is continued until the reaction is completed by chromatographic analysis. The mixture is concentrated in vacuo and diluted with water. The title product is isolated by filtration, washed with water (30 mL)

and dried in vacuo. The title product is identified by ¹HNMR and mass spectroscopy and analyzed by high pressure liquid chromatography to be >96% pure.

EXAMPLE 6

Preparation of 5-Ethyl-2,3-pyridinedicarboxylic acid using sulfuric acid

A mixture of 5-ethyl-2,3-pyridinedicarboxylic acid diethyl ester (25 g, 0.1 mol), sulfuric acid (30 g, 0.3 mol) and water (60 g, 3.3 mol) is heated at 70° to 110° C. A mixture of ethanol, water and hydrochloric acid is continuously distilled from the reaction mixture, and heating is continued until the reaction is complete by chromatographic analysis. The mixture is cooled to room temperature and the pH is adjusted to pH 1.3 to pH 2.0 with 50% sodium hydroxide. The title product is isolated by filtration, washed with water (20 mL) and dried in vacuo. The title product is identified by ¹HNMR and mass spectroscopy and analyzed by high pressure liquid chromatography to be >98% pure.

EXAMPLE 7

Preparation of 5-Ethyl-2,3-pyridinedicarboxylic acid using hydrochloric acid

A mixture of 5-ethyl-2,3-pyridinedicarboxylic acid diethyl ester (182 g, 0.73 mol), hydrochloric acid (93 g, 2.5 mol) and water (60 g, 3.3 mol) is heated at 70° to 110° C. A mixture of ethanol, water and hydrochloric acid is continuously distilled from the reaction mixture and replaced with 18% aqueous hydrochloric acid. The reaction mixture is held at this temperature until the reaction is complete by chromatographic analysis. The reaction mixture is cooled to room temperature and the pH is adjusted to pH 1.3 to pH 2.0 with 50% sodium hydroxide. The title product is isolated by filtration, washed with water (20 mL) and dried in vacuo. The title product is identified by ¹HNMR and mass spectroscopy and analyzed by high pressure liquid chromatography to be >96% pure.

EXAMPLE 8

Preparation of 5-Ethyl-2,3-pyridinedicarboxylic acid using hydrochloric acid and diglyme A mixture of 5-ethyl-2,3-pyridinedicarboxylic acid diethyl ester (44.2 g, 0.18 mol), hydrochloric acid (23.3 g, 0.64 mol) and water (103 g, 5.7 mol) is heated at 80° C. for 18 hours. The reaction mixture is cooled to 30° C. and washed with methylene chloride. Diglyme is added to the mixture and the mixture is concentrated in vacuo, diluted with methylene chloride and filtered. The filter cake is washed with diglyme and methylene chloride to give the hydrochloride salt of the title compound. The filter cake is then slurried with water, filtered and dried to give the title compound. The title product is identified by ¹HNMR and mass spectroscopy and analyzed by high pressure liquid chromatography to be >99% pure.

I claim:

1. A method for the preparation of a formula I 2,3-pyridine or quinolinedicarboxylic acid having the structure

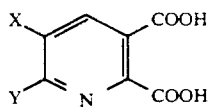

wherein

X and Y are each independently hydrogen, halogen, $C_1$–$C_6$ alkyl, $C_1$–$C_4$ hydroxyalkyl, $C_1$–$C_4$ alkoxyalkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino, $C_1$–$C_4$ alkylsulfonyl or phenyl optionally substituted with a $C_1$–$C_4$ alkyl, $C_1$–$C_4$ alkoxy or halogen group; and, when taken together, X and Y may form a ring in which XY is represented by the structure

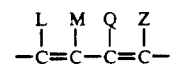

wherein L, M, Q and Z are each hydrogen, halogen, $C_1$–$C_4$ alkyl or $C_1$–$C_4$ alkoxy; which comprises hydrolyzing a formula II 2,3-pyridine or quinolinedicarboxylic acid diester having the structure

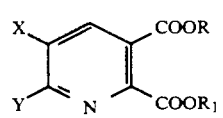

wherein R and $R_1$ each represent a $C_1$–$C_6$ alkyl group and X and Y are as described above for formula I; by heating said dicarboxylic acid diester in the presence of water and an acid having an ionization constant $pK_a$ of less than 3.0 at a temperature between about 50° C. and 110° C., separating water and alcohol from said reaction mixture, cooling the remaining reaction mixture to a temperature between about 20° C. and 35° C., treating the remaining reaction mixture with base, if the reaction mixture has a pH value less than pH 1.3, to adjust the pH of said mixture to a value between 1.3 and 2.0 and separating the formula I 2,3-pyridine or quinolinedicarboxylic acid from the pH adjusted mixture.

2. The method according to claim 1 wherein the acid employed in the hydrolysis is sulfuric, sulfurous, hydrochloric, hydrobromic, trifluoroacetic, trichloroacetic, β-naphthalene sulfonic, benzene sulfonic, p-toluene sulfonic, p-ethylbenzene sulfonic, dichloracetic or phosphoric acid and is used at about 3 to 5 molar equivalent per mole of diester treated.

3. The method according to claim 1 wherein the base is an aqueous solution of an alkali metal hydroxide.

4. The method according to claim 1 wherein the reaction mixture which has been adjusted to a pH value between pH 1.3 and pH 2.0 is filtered to obtain the formula I 2,3-pyridinedicarboxylic acid.

5. The method according to claim 1 wherein the acid is sulfuric, hydrochloric or hydrobromic acid and the base is sodium hydroxide.

6. The method according to claim 1 wherein the 2,3-pyridine or quinolinedicarboxylic acid is 5-ethyl-2,3-pyridinedicarboxylic acid, 5-methoxymethyl-2,3-pyridinedicarboxylic acid, 2,3-pyridinedicarboxylic acid, 5-methyl-2,3-pyridinedicarboxylic acid or 2,3-quinolinedicarboxylic acid; the acid is sulfuric, hydrochloric or hydrobromic acid and the base is sodium hydroxide.

7. A method for the preparation of an acid salt of a formula I 2,3-pyridine or quinolinedicarboxylic acid having the structure

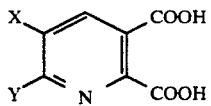  (I)

wherein

X and Y are each independently hydrogen, halogen, $C_1$-$C_6$ alkyl, $C_1$-$C_4$ hydroxyalkyl, $C_1$-$C_4$ alkoxyalkyl, $C_1$-$C_6$ alkoxy, $C_1$-$C_4$ alkylthio, phenoxy, $C_1$-$C_4$ haloalkyl, nitro, cyano, $C_1$-$C_4$ alkylamino, diloweralkylamino, $C_1$-$C_4$ alkylsulfonyl or phenyl optionally substituted with a $C_1$-$C_4$ alkyl, $C_1$-$C_4$ alkoxy or halogen group; and, when taken together, X and Y may form a ring in which XY is represented by the structure

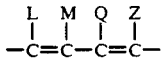

wherein L, M, Q, and Z are each hydrogen, halogen, $C_1$-$C_4$ alkyl or $C_1$-$C_4$ alkoxy; which comprises hydrolyzing a formula II 2,3-pyridine or quinolinedicarboxylic acid diester having the structure

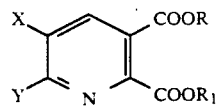  (II)

wherein R and $R_1$ each represent a $C_1$-$C_6$ alkyl group and X and Y are as described above for formula I, in the presence of water and an acid having a $pK_a$ of less than 3.0 at a temperature between about 50° C. and 110° C., cooling said heated mixture to a temperature between about 20° C. and 40° C., washing said cooled mixture with a volatile chlorinated hydrocarbon, an ether or a water-immiscible alcohol, adding to the washed mixture 1,1'-oxybis[2-methoxyethane]; 2,5,8,11-tetraoxadodecane or 2,5,8,11,14-pentaoxapentadecane and separating water to obtain the formula I 2,3-pyridine or quinolinedicarboxylic acid as the acid salt and optionally dispersing said acid salt in water or aqueous base to obtain the formula I 2,3-pyridine or quinolinedicarboxylic acid.

8. The method according to claim 7 wherein the 2,3-pyridine or quinolinedicarboxylic acid is 5-ethyl-2,3-pyridinedicarboxylic acid, 5-methoxymethyl-2,3-pyridinedicarboxylic acid, 2,3-pyridinedicarboxylic acid, 5-methyl-2,3-pyridinedicarboxylic acid or 2,3-quinolinedicarboxylic acid.

9. The method according to claim 7 wherein the acid used is hydrochloric acid and is used at about 1.5 to 5 molar equivalents of acid per mole of diester.

10. The method according the claim 7 wherein the volatile chlorinated hydrocarbon is dichloromethane, chloroform or carbon tetrachloride; the ether is diethyl ether or tetrahydrofuran; and the water-immiscible alcohol is n-butanol, n-hexanol or n-pentanol.

* * * * *